US00PP07799P

United States Patent [19]

White

[11] Patent Number: Plant 7,799

[45] Date of Patent: Feb. 18, 1992

[54] POINSETTIA PLANT NAMED MARJO CHARM

[75] Inventor: James White, Stouffville, Canada

[73] Assignee: Ball Seed Co., West Chicago, Ill.

[21] Appl. No.: 611,404

[22] Filed: Nov. 9, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A Poinsettia plant named Marjo Charm particularly described by its pink and white bicolored flowers, compact growth habit, freely branching habit, eight week flowering response, cyathia that abscise relatively early, ability to be finished at cool night temperatures which intensify bract color, good post-production longevity, and its resistance to bruising during shipping.

1 Drawing Sheet

The present invention relates to a new and distinct cultivar of Poinsettia plant known by the cultivar name Marjo Charm and botanically known as *Euphorbia pulcherrima*. This naturally occurring sport of Marjo Pink was first observed by me in the greenhouses of my business, James White Florist, Stouffville, Ontario, Canada, in 1984. It was propagated asexually by me in 1985 and flowered for three years to confirm its phenotypic stability.

Asexual reproduction by terminal cuttings taken at West Chicago, Ill. has also established that the unique features of Marjo Charm are stabilized and are reproduced true to type in successive propagations.

The following characteristics have been repeatedly observed and are determined to be basic characteristics of Marjo Charm which in combination distinguish this new Poinsettia from both its parent Marjo Pink and other cultivated Poinsettias of this type known and used in the floriculture industry.

1. Marjo Charm has pink and white bicolored bracts similar to Noel Blush. Marjo Pink has light pink bracts.
2. Marjo Charm is more compact than Noel Blush. Marjo Charm's leaf color and plant form are similar to Marjo Pink and Marjo White, the latter being disclosed in a pending plant patent application of applicant.
3. Marjo Charm is freely branching with five to seven branches upon pinching.
4. Marjo Charm is an eight week cultivar, flowering one week earlier than Noel Blush (9 week response). Marjo Charm flowers at the same time as Marjo Pink and Marjo White.
5. Marjo Charm has cyathia that abscise earlier than Noel Blush.
6. Marjo Charm can be finished at a cool night temperature of 55° to 58° F. which intensifies bract color.
7. Marjo Charm has good post-production longevity and is resistant to bruising during shipping.

The accompanying colored photograph illustrates the overall appearance of this cultivar, showing colors as true as reasonably possible to obtain in a colored reproduction of this type.

Marjo Charm has not been observed under all possible environmental conditions. The phenotype may vary significantly with variations in environment such as temperature, light intensity and daylength.

The following is a detailed description of my new Poinsettia cultivar, Marjo Charm, based on plants produced under commercial practice in West Chicago, Ill., in a glass covered greenhouse with day temperatures of 70° to 76° F. and night temperatures of 60° to 65° F.

Color references are made to The Royal Horticultural Society Colour Chart except where general terms of ordinary dictionary significance are used.

Classification:

A. *Botanical.*—*Euphorbia pulcherrima.*

B. *Commercial.*—Poinsettia.

Parentage: Naturally occurring sport of Marjo Pink.

Propagation:

A. *Type cutting.*—Terminal.

B. *Time to initiate roots.*—9 days at 75° F. summer; 12 days at 70° F. winter.

C. *Rooting habit.*—Excellent; well branched.

Plant description:

A. *Form.*—Freely branching, upright.

B. *Habit of growth.*—Compact.

C. *Foliage description.*—1. Size: Length, 9 to 12 cm; width, 6 to 8 cm. 2. Shape: Ovate-elliptic, some fiddle-shaped, tips acuminate. 3. Texture: Smooth. 4. Margin: Entire to lobed (fiddle-shaped). 5. Color: Mature foliage, upper surface 147A; lower surface 147B. Young foliage, upper surface 147B; lower surface 147C.

Flowering description:

A. *Flowering habits.*—Many cyanthia within inflorescences that are arranged as an umbel-like cyme. Large showy bracts.

B. *Natural flowering season.*—Eight week cultivar, flowering naturally the second week of November.

C. *Bracts.*—1. Shape: Ovate with entire, sinnuate or repand margin. 2. Size: Length, 8 to 11 cm; width, 6 to 8 cm. 3. Number: Ranges from 15 to 20 per inflorescence. 4. Color: Upper surface, mature: 54B and 54C; at margins, 157A. Lower surface, mature: Center of bracts, 54C and 54D; at margins, 157B.

D. *Cyathia.*—1. General description: Initially three main flowering stems with subsequent lateral cyathia development. 2. Borne: Upright as an umbel-like cyme. 3. Quantity: Average quantity; may abscise prematurely. 4. Color: 7B.

Reproductive organs: Typical for *Eurphorbia pulcherrima* cultivars, not significant.

Disease resistance: No fungal or bacterial problems observed to date.

I claim:

1. A new and distinct cultivar of Poinsettia plant named Marjo Charm, as illustrated and described.

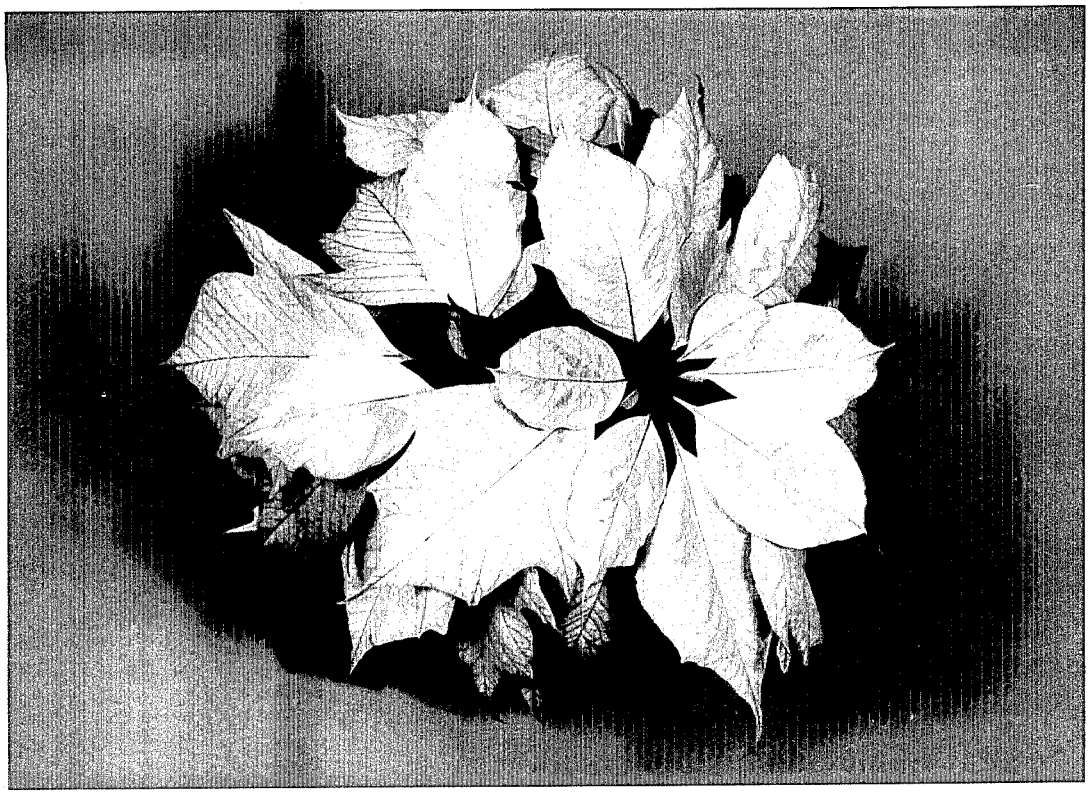

* * * * *